United States Patent
Engelbrecht et al.

(10) Patent No.: US 7,144,927 B1
(45) Date of Patent: Dec. 5, 2006

(54) PHOTOINITIATOR SYSTEM WITH ACYLPHOSPHINE OXIDE INITIATORS

(75) Inventors: Juergen Engelbrecht, Elmshorn (DE); Gunther Groeger, Elmshorn (DE); Wolfram Ziegler, Elmshorn (DE)

(73) Assignee: S & C Polymer Silicon-und Composite-Spezialitaten GmbH, Elmshorn (DE)

( * ) Notice: Subject to any disclaimer, the term of this patent is extended or adjusted under 35 U.S.C. 154(b) by 112 days.

(21) Appl. No.: 10/148,745

(22) PCT Filed: Nov. 16, 2000

(86) PCT No.: PCT/EP00/11405

§ 371 (c)(1), (2), (4) Date: Aug. 21, 2002

(87) PCT Pub. No.: WO01/44873

PCT Pub. Date: Jun. 21, 2001

(30) Foreign Application Priority Data

Dec. 17, 1999 (DE) .................................. 199 61 347

(51) Int. Cl.
- C08F 2/46 (2006.01)
- A61F 2/00 (2006.01)
- A61C 5/00 (2006.01)

(52) U.S. Cl. .................. 522/25; 522/28; 522/100; 523/113; 523/117; 523/118; 433/228.1

(58) Field of Classification Search .................. 522/25, 522/28, 100; 523/113, 117, 118
See application file for complete search history.

(56) References Cited

U.S. PATENT DOCUMENTS

| 4,916,805 A | 4/1990 | Guggenberger et al. |
| 6,054,007 A * | 4/2000 | Boyd et al. .................. 156/245 |
| 6,355,704 B1 * | 3/2002 | Nakatsuka et al. .......... 523/116 |

FOREIGN PATENT DOCUMENTS

| EP | 0 738 928 A | 10/1996 |
| EP | 0 879 829 A | 11/1998 |
| GB | 2 292 740 A | 3/1996 |
| GB | 2 310 855 A | 10/1997 |

\* cited by examiner

*Primary Examiner*—Tae H. Yoon
(74) *Attorney, Agent, or Firm*—Frommer Lawrence & Haug LLP; Ronald R. Santucci

(57) ABSTRACT

A visible light photopolymerizable composition comprising a) an aryliodonium salt and b) an acylphosphine oxide compound. These compositions can be used together with an epoxy resin as a dental composition.

16 Claims, No Drawings

PHOTOINITIATOR SYSTEM WITH ACYLPHOSPHINE OXIDE INITIATORS

FIELD OF THE INVENTION

This invention relates to compositions comprising an aryliodonium salt and an acylphosphine oxide derivative. The invention especially refers to corresponding dental compositions which may additionally comprise a cationally polymerizable epoxy compound or resin.

BACKGROUND OF THE INVENTION

Epoxy compounds have previously been cured by various cationic initiator systems. U.S. Pat. No. 4,256,828 describes photocopolymerizable compositions containing epoxides, organic material with hydroxyl functionality, and a photosensitive aromatic sulfonium or iodonium salt of a halogen-containing complex ion. This patent also describes coated substrates. U.S. Pat. No. 4,250,053 describes sensitized aromatic iodonium or aromatic sulfonium salt photoinitiator systems for cationic reactions. U.S. Pat. No. 4,026,705 describes epoxy compositions that can be cured with visible radiant energy based on the use of certain organic dyes in combination with diarylhalonium salts. Cationic polymerization of various olefinic and cyclic organic compounds and organosilicon cyclics is also described. WO 95/30402 describes systems of iodonium salts and ferrocenium salt for visible light cure of epoxides. U.S. Pat. No. 5,856,373 describes systems of iodonium salts and visible light sensitizers that yield in sufficient cure in the presence of hydroxyl-containing materials.

SUMMARY OF THE INVENTION

The present invention provides a composition comprising a) an aryliodonium salt and b) an acylphosphine oxide compound. This composition can additionally comprise c) a cationically polymerizable epoxy compound (like a monomer) or resin.

DETAILED DESCRIPTION

It has been surprisingly found that the photoinitiator compositions of the present invention can be used as photoinitiators for systems which comprise cationically polymerizable epoxy resins: Such systems can be cured using visible light cure techniques. Previous initiators provided rapid cure only for thin epoxy-based resin samples, such as utilized in coating and film technologies. Additionally, powerful and potentially harmful sources of UV-radia-tion were previously required to achieve polymerization to a significant depth. Using visible light sources the present invention achieves enhanced depth of cure in a surprisingly short time, so that safer and less expensive equipment may now be utilized to cure epoxy resins to thicknesses not previously attainable. Furthermore, the new initiator combination of aryliodonium salts and acylphosphine oxide is new, very efficient and not depending on using compounds containing hydroxyl groups described in U.S. Pat. No. 5,856,373 which yields in non desirable high amounts of water sorption when used under humid conditions.

The photoinitiator systems and the photopolymerizable compositions of the invention are sensitive to visible light, and photocure rapidly, without the use of heat, to polymers having desirable properties. For purposes of the present invention, visible light is defined as light having a wavelength of between about 400 and 700 nanometers. The photopolymerization of the compositions of the invention occurs on exposure of the compositions to any source of radiation emitting actinic radiation at a wavelength within the visible spectral region. Exposures may be from less than about 1 second to 10 minutes or more, depending upon the amounts and particular components of the compositions utilized and depending upon the radiation source and distance from the source and the thickness of the composition to be cured. The compositions of the invention are one-part, stable compositions having very good shelf life and good thermal stability.

The cationically polymerizable epoxy resins useful in the compositions of the invention comprise organic compounds having an oxirane ring, i.e.,

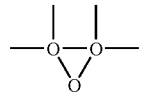

polymerizable by ring opening. Such materials, broadly called epoxides, include monomeric epoxy compounds and epoxides of the polymeric type and can be aliphatic, cycloaliphatic, aromatic or heterocyclic. These materials generally have, on the average, at least 1 polymerizable epoxy group per molecule, and preferably at least about 1.5 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures containing one, two, or more epoxy groups per molecule. The "average" number of epoxy groups per molecule is determined by dividing the total number of epoxy groups in epoxy-containing material by the total number of epoxy molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic cure at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as the epoxycyclohexanecarboxylates, typified by 3,4-epoxycyclohexylm-ethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, incorporated herein by reference.

Further epoxy-containing materials which are particularly useful in the practice of this invention include glycidyl ether monomers of the formula

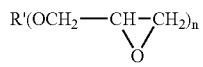

where R' is alkyl, especially $C_1$–$C_6$ alkyl, or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type which can be used in the practice of this invention are described in U.S. Pat. No. 3,018,262, incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "UVR 6110" or "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxy-cyclopentyl) ether (e.g., "ERL-0400" from Union Carbide Corp.), aliphatic epoxy modified with polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.). bis(3,4-epoxy-cyclohexyl)adipate (e.g., "ERL-4299" or "UVR-6128", from Union Carbide Corp.), 2-(3,4-epoxycyclohexyl-5,5-spiro-3,4-epoxy)cyclohexane-meta-dioxane (e.g., "ERL-4234" from Union Carbide Corp.), vinylcyclohexene monoxide (from Union Carbide Corp.), 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-tert butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis>4-(2, 3-epoxypropoxy)-phenyl fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, e.g., epichlorohydrin; alkylene oxides, e.g., propylene oxide, styrene oxide; alkenyl oxides, e.g., butadiene oxide; glycidyl esters, e.g., ethyl glycidate.

Other useful epoxy resins are silicones with epoxyfunctionality, especially cyclohexylepoxy groups, especially those with a silicone backbone. Examples are UV 9300, UV 9315, UV 9400, UV 9425, all delivered by GE Bayer Silicones.

The amounts of the cationically polymerizable epoxy compounds or resins useful in the photopolymerizable compositions of the invention may vary over broad ranges. Preferred amounts are 40 to 99.98% by weight, more preferred amounts are 80 to 99.9% by weight and especially preferred amounts are 90 to 99% weight of the photopolymerizable composition.

The polymers of the epoxy resin may optionally contain other functionalities that do not substantially interfere with cationic cure at room temperature.

Blends of various epoxy-containing materials are particularly contemplated in this invention. Examples of such blends include two or more molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical nature, such as aliphatic and aromatic, or functionality, such as polar and non-polar. Other cationically polymerizable monomers or polymers may additionally be incorporated.

Hydroxyl-containing materials can be added but are not a necessary embodiment of the invention. If they are used they may be any liquid or solid organic material having hydroxyl functionality.

Preferably the hydroxyl-containing material contains two or more primary or secondary aliphatic hydroxyl groups (i.e., the hydroxyl group is bonded directly to a non-aromatic carbon atom). The hydroxyl group may be terminally situated, or they may be pendent from a polymer or copolymer. The molecular weight of the hydroxyl-containing organic material may vary from very low (e.g., 32) to very high (e.g., one million or more). Suitable hydroxyl-containing materials may have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl-containing material may optionally contain other functionalities that do not substantially interfere with cationic cure at room temperature. Thus, the hydroxyl-containing materials may optionally be nonaromatic in nature or may comprise aromatic functionality. The hydroxyl-containing material may optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material may, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known to the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis (hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds such as N,N-bis(hydroxyethyl) benzamide; 2-butyne-1,4-diol; 4,4'-bis(hydroxymethyl) diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols of molecular weights from about 200 to about 10,000 corresponding to equivalent weight of 100 to 5000 for the diols or 70 to 3300 for triols; polytetramethylene ether glycols (polytetrahydrofuran "poly THF") of varying molecular weight; copolymers of hydroxypropyl and hydroxyethyl acrylates and methacrylates with other free radical-polymerizable monomers such as acrylate esters, vinyl halides; or styrene; copolymers containing pendent hydroxy groups formed by hydrolysis or partial hydrolysis of vinyl acetate copolymers, polyvinylacetal resins containing pendent hydroxyl groups; modified cellulose polymers such hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "Terathane" series (available from du Pont de Nemours) of polytetramethylene ether glycols such as "Terathane" 650, 1000, 2000 and 2900; "PeP" (available from Wyandotte Chemicals Corporation) of polyoxyalkylene tetrols having secondary hydroxyl groups such as "PeP" 450, 550 and 650; "Butvar" series (available from Monsanto Chemical Company) of polyvinylacetal resins such as "Butvar" B-72A, B-73, B-76, B-90 and B-98; and "Formvar" 7/70, 12/85, 7/95S, 7/95E, 15/95S and 15/95E; "Tone" series (available from Union Carbide) of polycaprolactone polyols such as "Tone" 0200, 0210, 0230, 0240, 0300; "Paraplex U-148" (available from Rohm and Haas), and aliphatic polyester diol; "Multron" R series (available from Mobay Chemical Co.) of saturated polyester polyols such as "Multron" R-2, R-12A, R-16, R-18, R-38, R-68 and R-74; "Klucel E" (available from Hercules Inc.) a hydroxypropylated cellulose having an equivalent weight of approximately 100; and "Alcohol Soluble Butyrate" (available from Eastman Kodak) a cellulose acetate butyrate ester having a hydroxyl equivalent weight of approximately 400; polyether polyols such as polypropylene glycol diol (e.g., "Arcol PPG-425", "Arcol PPG-725", "Arcol PPG-1025", "Arcol PPG-2025", Arcol PPG-3025", "Arcol PPG-4025" from ARCO Chemical Co.); polypropylene glycol triol (e.g., "Arcol LT-28", "Arcol LHT-42", "Arcol LHT 112", "Arcol LHT 240", "Arcol LG-56", "Arcol LG-168", "Arcol LG-650" from ARCO Chemical Co.); ethylene oxide capped polyoxypropylene triol or diol (e.g., "Arcol 11-27", "Arcol 11-34", "Arcol E-351", "Arcol E-452", "Arcol E-785", "Arcol E-786" from ARCO Chemical Co.); ethoxylated bis-phenol A; propylene oxide or ethylene oxide-based polyols (e.g., "Voranol" polyether polyols such as "Voranol 230-056", "Voranol 220 series", "Voranol 230 series", "Voranol 240 series" from the Dow Chemicals Co.).

The amount of hydroxyl-containing organic material which may be used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like. Preferred amounts are up to 20% by weight, especially preferred amounts are 0.5 to 5% by weight of the photopolymerizable compositions.

Blends of various hydroxyl-containing materials are also contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material may contain a blend of hydroxyl-containing materials having different chemical nature, such as aliphatic and aromatic, or functionality, such as polar and non-polar. As an additionally example, one may use mixtures of two or more poly-functional hydroxy materials or one or more mono-functional hydroxy materials with poly-functional hydroxy materials.

The photopolymerizable (photocurable) composition of the present invention may additionally comprise a radically curable monomer or resin.

Such radically curable monomers or resins can, for example, be selected from acrylates, vinyl benzene derivatives, allyl derivatives, vinyl ketones.

Addition of vinylether compounds to the epoxy resin may be useful to speed up the photocure or trigger the desired physical properties of the final cured composition. Examples of vinylether compounds are Rapicure DVE-3 (triethyleng-lykoldivinylether), Rapicure CHVE (1,4-cyclohexan dimethanoldivinylether) and Rapicure HBVE (butandiol-monovinylether), all available from ISP Global Technologies Deutschland GmbH, Frechen, Germany. The ratio of epoxy compounds or resins to radically curable monomers or resins can be 10:90 to 90:10 based on the weight of the mixture of these components.

The aromatic iodonium complex salts or aryliodonium salts are of the formula:

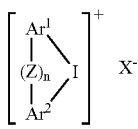

where $Ar^1$ and $Ar^2$ are aromatic groups having 4 to 20 carbon atoms and can, for example, be selected from the group consisting of phenyl, thienyl, furanyl and pyrazolyl groups; Z can, for example, be selected from the group consisting of oxygen; sulfur;

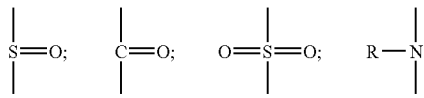

where R is aryl (of 6 to 20 carbons, such as phenyl) or acyl (of 2 to 20 carbons, such as acetyl, benzoyl, and the like.); a carbon-to-carbon bond; or

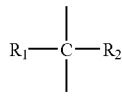

where $R_1$ and $R_2$ are selected from hydrogen, alkyl radicals of 1 to 4 carbons, and alkenyl radicals of 2 to 4 carbons; and n is zero or 1; and wherein X– is a halogen-containing complex anion which can, for example, be selected from tetrafluoroborate, hexafluorophosphate, hexafluoroarsenate, and hexafluoroantimonate.

The aromatic iodonium cations are stable and are well known and recognized in the art. See for example, U.S. Pat. Nos. 3,565,906; 3,712,920; 3,759,989; and 3,763,187; F. Beringer, et al., Diaryliodonium Salts IX, J. Am. Chem. Soc. 81, 342–51 (1959) and F. Beringer, et al., Diaryliodonium Salts XXII, J. Chem. Soc. 1964, 442–51; F. Beringer, et al., Iodonium Salts Containing Heterocyclic Iodine, J. Org. Chem. 30, 1141–8 (1965).

Representative $Ar^1$ and $Ar^2$ groups are aromatic groups having 4 to 20 carbon atoms selected from phenyl, thienyl, furanyl, and pyrazolyl groups. These aromatic groups may optionally have one or more fused benzo rings (e.g., naphthyl and the like; benzothienyl, dibenzothienyl; benzofuranyl, dibenzofuranyl; and the like.). Such aromatic groups may also be substituted, if desired, by one or more of the following non-basic groups which are essentially non-reactive with epoxide vinylether or hydroxy: halogen, nitro, N-arylamino groups, ester groups (e.g., alkoxycarbonyl such as methoxycarbonyl and ethoxycarbonyl, phenoxycarbonyl), sulfo ester groups (e.g., alkoxysulfonyl such as methoxysulfonyl and butoxysulfonyl, phenoxysulfonyl, and the like), amido groups (e.g., acetamido, butyramido, ethylsulfonamido, and the like), carbamyl groups (e.g., carbamyl, N-alkylcarbamyl, N-phenylcarbamyl, and the like), sulfamyl groups (e.g., sulfamyl, N-alkylsulfamyl, N,N-dialkylsulfamyl, N-phenylsulfamyl, and the like), alkoxy groups (e.g., methoxy, ethoxy, butoxy, and the like), aryl groups (e.g., phenyl), alkyl groups (e.g., methyl, ethyl, butyl, and the like), aryloxy groups (e.g., phenoxy) alkylsulfonyl (e.g., methylsulfonyl, ethylsulfonyl, and the like), arylsulfonyl groups (e.g., phenylsulfuonyl groups), perfluoroalkyl groups (e.g., trifluoromethyl, perfluoroethyl, and the like), and perfluoroalkysulfonyl groups (e.g., trifluoromethylsulfonyl, perfluorobutylsulfonyl, and the like).

Suitable examples of the aromatic iodonium complex salt photoinitiators include: diphenyliodonium tetrafluoroborate; di(4-methylphenyl)iodonium tetrafluoroborate; phenyl-4-methylphenyl-iodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)-iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; di(2, 4-dichlorophenyl)-iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate and di(2-benzothienyl) iodonium hexafluorophosphate.

Of the aromatic iodonium complex salts which are suitable for use in the compositions of the invention the preferred salts are the diaryliodonium hexafluorophosphate and the diaryliodonium hexafluoroantimonate. These salts are preferred because, in general, they are more thermally stable, promote faster reaction, and are more soluble in inert organic solvents than are other aromatic iodonium salts of complex ions.

The aromatic iodonium complex salts may be prepared by metathesis of corresponding aromatic iodonium simple salts (such as, for example, the diphenyliodonium bisulfate) in accordance with the teachings of Beringer, et al., J. Am. Chem. Soc 81, 342 (1959).

The aryliodonium complex salt is preferably present in the photoinitiator composition in amounts of about 10 to 90% by weight, preferably of about 30 to 70% by weight and most preferably of about 40 to 60% by weight. It is preferably present in the photopolymerizable composition in amounts of about 0.01–10% by weight, more preferably of about 0.02–5% by weight, and most preferably of about 0.05–4% by weight.

The (di)aryliodonium salts alone are not initiating the light cure of epoxy resins.

The sensitizer of the invention are acylphosphine oxide compounds or derivatives. Acylphosphine oxide senzitizers are described in EP 0 007 508, EP 0 057474, EP 0 073413 and DE 36 33 436 and known for their ability as initiators for acrylic resins. Nothing is described about their ability to act as a sensitizer for diaryliodonium compounds. Preferably the acylphosphinoxide compound is an acyldiphenylphosphine oxide like diphenyl(2,4,6-trimethylbenzoyl)phosphinoxide ("Lucirin® TPO", BASF) or a diacylphenylphosphinoxide like Bis(2,4,6-Trimethylbenzoyl)-phenylphosphinoxide (Irgacure 819, Ciba).

The sensitizer is selected based in part upon shelf stability considerations. Accordingly, selection of a particular sensitizer may depend to some extent upon the particular epoxy, vinyl ether, hydroxy-containing material and iodonium salt chosen.

By way of example, a preferred class of acylphosphine oxide sensitizers has the formula:

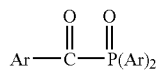

where Ar is an aromatic group which may be the same or different.

The visible light sensitizer is preferably present in the photoinitiator composition in amounts of about 10 to 90% by weight, preferably of about 30 to 70% by weight and most preferably of about 40 to 60% by weight. It is preferably present in the photopolymerizable composition in amounts of about 0.01–10% by weight, more preferably of about 0.02–5% by weight, and most preferably of about 0.05–4% by weight.

The photopolymerizable compositions of the invention are prepared by simply admixing, under "safe light" conditions, the components of the inventive compositions. Suitable inert solvents may be employed if desired when effecting this mixture. Examples of suitable solvents are acetone and acetonitrile, and include any solvent which does not react appreciably with the components of the inventive compositions. A liquid material to be polymerized may be used as a solvent for another liquid or solid material to be polymerized. Solventless compositions can be prepared by simply dissolving the aromatic iodonium complex salt and sensitizer in the epoxy resin or vinyl ether with or without the use of mild heating.

Dental applications particularly benefit from the present invention. Until now, acrylate and methacrylate chemistry has been used extensively for adhesive and restorative dental compositions. This chemistry advantageously can be cured with visible light using photoinitiator systems. However, this chemistry has the disadvantage of a relatively high degree of shrinkage during the polymerization process. In contrast, during polymerization, the epoxy resins of the present invention shrink significantly less than the acrylate and methacrylate resins of the prior art. The present invention provides a system for curing epoxy resins in an acceptable time frame and to sufficient depth using visible light source equipment already available in the dental office.

The dental materials of the present invention may be filled or unfilled and include dental materials such as direct esthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein will refer to the placing of a dental material in temporary or permanent bonded (e.g., adhesive) or touching (e.g., occlusal or proximal) contact with a natural tooth. The term "composite" as used herein will refer to a filled dental material. The term "restorative" as used herein will refer to a composite which is polymerized after it is disposed adjacent to a tooth. The term "prosthesis" as used herein will refer to a composite which is shaped and polymerized for its final use (e.g., as crown, bridge, veneer, inlay, onlay or the like) before it is disposed adjacent to a tooth. The term "sealant" as used herein will refer to a lightly filled composite or to an unfilled dental material which is cured after it is disposed adjacent to a tooth. "Polymerizable", as used herein, refers to curing or hardening the dental material, e.g., by free-radical, ionic or mixed reaction mechanisms.

In certain applications, the use of a filler may be appropriate. The choice of filler affects important properties of the composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. Epoxy resin compositions of the invention, either alone or in admixture with diluent monomer, can be prepared with refractive indices which approach or approximate the refractive indices of fillers such as quartz (refractive index 1.55), submicron silica (1.46), and 5.5:1 mole ratio $SiO_2:ZrO_2$ non-vitreous micro-particles (1.54). In this way the appearance of the dental material can, if desired, be made to closely approximate the appearance of natural dentition.

Radiopacity is a measurement of the ability of the composite to be detected by x-ray examination. Frequently a radiopaque composite will be desirable, for instance, to enable the dentist to determine whether or not a filling remains sound. Under other circumstances a non-radiopaque composite may be desirable.

The amount of filler which is incorporated into the composite (referred to herein as the "loading level" and expressed as a weight percent based on the total weight of the dental material) will vary depending on the type of filler, the epoxy resin and other components of the composition, and the end use of the composite.

For some dental materials (e.g., sealants), the epoxy resin compositions of the invention can be lightly filled (e.g., having a loading level of less than about 40 weight percent) or unfilled. Preferably the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level of between about 70 and 90 weight percent is generally preferred.

Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or nonradiopaque.

Examples of suitable inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Metallic fillers may also be incorporated, such as particulate metal filler made from a pure metal such as those of Groups IVA, VA, VIA, VIIA, VIII, IB, or IB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glasses have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as epoxies, vinylethers, acrylates, methacrylates and the like. Examples of coupling agents include glycidyltrimethoxysilane, O(vinyloxyethyl)-N-(triethoxysilylpropyl)urethane, gamma-methacryloxypropyltrimethoxysilane, gamma-mercaptopropyltriethoxysilane, gamma-aminopropyltrimethoxysilane, beta-(3,4-epoxycyclohexyl)ethyltrimethoxysilane, and the like.

The dental materials of the present invention can also contain suitable adjuvants such as accelerators, inhibitors, absorbers, stabilizers, pigments, dyes, viscosity modifiers, surface tension depressants and wetting aids, antioxidants, and other ingredients well known to those skilled in the art.

The amounts and types of each ingredient in the dental material should be adjusted to provide the desired physical and handling properties before and after cure. For example, the cure rate, cure stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

When the dental material is applied to a tooth, the tooth can optionally be pre-treated with a primer such as dentin or enamel adhesive by methods known to those skilled in the art.

Particularly useful compositions of the present invention are visible-light photopolymerizable dental composition useful for polymerization in the oral environment. These compositions comprise a) a cationically polymerizable epoxy resin, b) an aryliodonium salt, c) an acylphosphine oxide and optionally d) a dental filler present in the composition. These components are present in amounts sufficient to provide cure of said photo-polymerizable resin by exposure to visible light to a cure depth of at least about 1 mm. The compositions may additionally comprise cationically curable resins selected from oxetanes, oxolanes, cyclic acetals, lactams, lactones and vinyl ethers. The compositions may additionally comprise radically curable resins selected from acrylates, methacrylates, allyl compounds, vinyl benzene compounds or other unsaturated compound suitable for radical polymerisation.

The inventive compositions can be used for the restauration of teeth and for fixing brackets, crowns, prostheses or inlays in teeth. Unless otherwise indicated, all parts and percentages are by weight, and all molecular weights are weight average molecular weight.

The compositions of the invention are as well very useful for industrial applications, e.g. for coatings on metal, glass, fabrics, paper, creating negative print reliefs for the printing industry, conductive plates, visible light cure glues or sealants, building up moulds by visible light. An important advantage is the deeper depth of cure in comparison to UV light, especially in pigmented systems and the less harmfulness of visible light.

EXAMPLES

Example 1

A mixture of 19.5 grams epoxy resin ERL4221 fom Union Carbide, 4.5 grams vinylether DVE-3 from ISP TECHNOLOGIES, INC., 0.1800 grams LUCIRIN TPO and 0.2935 grams of (4-n-Dodecyloxyphenyl)-phenyliodonium-hexafluoroantimonate was combined and stirred in the absence of light. 5.60 grams of the above obtained light curable epoxy system was filled with 12 grams of a silane-treated filler (Barium-Glas GM27884 SCHOTT Landshut). The composite is stable at room temperature in the absence of light.

Example 2

A mixture of 19.5 grams epoxy resin ERL4221 fom Union Carbide, 4.5 grams vinylether DVE-3 from ISP TECHNOLOGIES, INC., 0.1800 grams LUCIRIN TPO and 0.2935 grams of (4-n-Dodecyloxyphenyl)phenyliodonium-hexafluoroantimonate was combined and stirred in the absence of light. 5.60 grams of the above obtained light curable epoxy system was filled with 12 grams of a silane-treated filler (F-Quarz-066, Industrial Corporation). The composite is stable at room temperature in the absence of light.

Example 3

A mixture of 19.5 grams epoxy resin ERL4221 fom Union Carbide, 4.5 grams vinylether DVE-3 from ISP TECHNOLOGIES, INC., 0.1800 grams LUCIRIN TPO and 0.7235 grams of (4-n-Dodecyloxyphenyl)-phenyliodonium-hexafluoroantimonate was combined and stirred in the absence of light. 5.60 grams of the above obtained light curable epoxy system was filled with 13 grams of a silane-treated filler (SILBOND FW12 EST, Quarzwerke). The composite is stable at room temperature in the absence of light.

Example for Acylphosphine Catalyst Mixture

A catalyst mixture is prepared by dissolving 7.2 g (4-n-Dodecyloxyphenyl)phenyliodoniumhexafluoroantimonat and 1.8 g Lucirin TPO in 10 g ethylacetate (thoroughly stirring in the absence of light).

This catalyst mixture is able to harden the mentioned monomers. For example, 1.90 g of this catalyst mixture is able to cure a monomer mixture of 9.75 g epoxy resin ERL4221 (Union Carbide) and 2.2 g vinylether DVE-3 (ISP Technologies) to a depth of cure of 6.4 mm (90s, lamp: Kulzer UniXS).

TABLE 1

| | Example 1 | Example 2 | Example 3 |
|---|---|---|---|
| Starter: | TPO/Iodonium | TPO/Iodonium | TPO/Iodonium |
| Monomer: | ERL 4221/DVE-3 | ERL 4221/DVE-3 | ERL 4221/DVE-3 |
| Filler: | Ba-Glas (epoxidized) | F-Quarz (epoxidized) | Silbond FW12EST |
| Depth of Cure 1 min light cure [mm] | 2.8 | 3.7 | 6.0 |
| Translucency 2 mm | very good | low | very low |
| Transverse strength [MPa] | 68 | 36 | 59 |
| Compressive strength [N/mm2] | 160 | 190 | 120 |
| Diamet. tensile strength [N/mm2] | 28 | 34 | 25 |
| Estetic | toothlike | opaque | greyopaque |

The examples show similar mechanical strength like widely used light cure compositions based on methacrylate resins.

The invention claimed is:

1. A method of making a modified dental material wherein the modification comprises adding a composition comprising:
   a) a photoinitiator which consists of at least one aryliodonium salt and at least one acylphosphine oxide derivative, and
   b) at least one cationically polymerizable epoxy compound or resin, during the process of making a dental material to form the modified dental material.

2. The method according to claim 1, wherein said aryliodonium salt is a diaryliodonium salt.

3. The method according to claim 1, wherein the aryliodonium salt is a diaryliodonium hexafluorophosphate or a diaryliodonium hexafluoroantimonate.

4. The method according to claim 1, wherein said acylphosphine oxide derivative is selected from the group consisting of acyldiphenylphosphine oxide and diacylphenylphosphine oxide.

5. The method according to claim 1, said composition comprising an additional cationically curable compound or resin other than an epoxy compound or resin.

6. The method according to claim 5, wherein said additional cationically curable coumpound or resin is selected from the group consisting of oxetanes, oxolanes, cyclic acetals, lactams, lactones, and vinyl ethers.

7. The method according to claim 1, said composition comprising an additional radically curable compound or resin.

8. The method according to claim 7, wherein said additional radically curable resin is selected from the group consisting of acrylates, vinyl benzene compounds, allyl compounds, vinyl ketones.

9. The method according to claim 1, said composition additionally comprising:
   b) at least one filler, and/or
   c) at least one radiopaque filter.

10. The method according to claim 9, wherein the filler is an inorganic or a cross-linked organic material or a mixture thereof.

11. The method according to claim 1, wherein the composition is a polymerized composition.

12. The method according to claim 11, wherein said polymerized composition has a thickness greater than 1 mm.

13. The method according to claim 1 for the restoration of teeth.

14. The method according to claim 1 for fixing brackets, crowns, prostheses or inlays.

15. The method of claim 1 wherein, b) is at least one cationically polymerizable epoxy compound.

16. The method of claim 1 wherein, b) is at least one resin.

* * * * *